United States Patent [19]

Waller

[11] 4,414,409

[45] Nov. 8, 1983

[54] PALLADIUM SULFONATE CATALYST SYSTEMS FOR CARBONYLATION OF OLEFINS

[75] Inventor: Francis J. Waller, Wilmington, Del.

[73] Assignee: E. I. Du Pont de Nemours & Company, Wilmington, Del.

[21] Appl. No.: 333,178

[22] Filed: Dec. 21, 1981

[51] Int. Cl.³ ................... C07C 51/14; C07C 67/38
[52] U.S. Cl. .................. 560/233; 260/410.5; 260/410.9 R; 260/413; 260/465.4; 560/114; 560/204; 562/497; 562/522
[58] Field of Search ............ 260/410.9 R, 413, 465.4, 260/410.5; 560/114, 204, 233; 562/497, 522, 590

[56] References Cited

U.S. PATENT DOCUMENTS

| | | | |
|---|---|---|---|
| 3,437,676 | 4/1969 | von Kutepow et al. | 260/468 |
| 3,501,518 | 3/1970 | von Kutepow et al. | 260/468 |
| 3,641,074 | 2/1972 | Fenton | 260/410.9 |
| 3,674,831 | 7/1972 | Rennick | 560/114 |
| 3,723,486 | 3/1973 | Kajimoto et al. | 260/410.9 R |
| 3,793,369 | 2/1974 | Hara et al. | 260/497 A |
| 3,839,378 | 10/1974 | Yamaguchi et al. | 260/413 |
| 3,965,132 | 6/1976 | Norell | 260/410.9 R |
| 4,179,402 | 12/1979 | Kim | 560/233 |
| 4,179,403 | 12/1979 | Kim | 560/233 |
| 4,292,437 | 9/1981 | Squire | 560/233 |

OTHER PUBLICATIONS

Booth et al., *J. Chem. Soc. Perkin I*, 2441, (1979).
Cavinato et al., *J. Mol. Catalysis*, 10, 161, (1981).
Tsuji, *Accounts Chem. Res.*, 2, 144, (1969).

*Primary Examiner*—Michael L. Shippen

[57] ABSTRACT

Carbonylation of olefins is carried out in the presence of a hydroxylic compound, carbon monoxide and a catalyst system comprising an organic phosphine liganded palladium compound and a perfluorosulfonic acid.

14 Claims, No Drawings

PALLADIUM SULFONATE CATALYST SYSTEMS FOR CARBONYLATION OF OLEFINS

FIELD OF THE INVENTION

This invention relates to palladium catalyzed carbonylation of olefinically unsaturated compounds in the presence of a perfluorosulfonic acid.

BACKGROUND INFORMATION

Carbonylation of olefins under mild conditions with minimum by-product formation based on palladium complex salts as catalysts, examples of which include palladium catalysts containing phosphines, phosphites, ammonia, amines, nitriles, and unsaturated hydrocarbons as ligands, is known.

Tsuji, *Accounts Chem. Res.* 2, 144–152 (1969) reviews palladium catalyzed carbon-carbon bond formation, including such carbonylation reactions. Bittler, et al., *Agnew. Chem. Internat. Edit.,* 7, 329–335 (1968) disclose carbonylation of olefins under mild conditions in the presence of complex palladium (II) compounds and observe the Pd(O) compounds are inactive in the absence of added hydrogen chloride.

Several references disclose that certain metal halides, when added to the reaction mixture, improve the yield of linear products relative to branched products. These include, e.g., Mrowca, U.S. Pat. No. 4,257,973; Mrowca, U.S. Pat. No. 3,859,319; Butter, U.S. Pat. No. 3,700,706; Knifton, U.S. Pat. No. 3,919,272; and Knifton, *J. Org. Chem.,* 41, 2885–2890 (1976). Use of such halides may pose corrosion problems. Fenton, U.S. Pat. No. 3,641,074 discloses the use of hydrogen and/or limiting mineral acid content of the reaction medium to favor the formation of linear rather than branched products.

Kajimoto, et al., U.S. Pat. No. 3,723,486 disclose the use of a palladium complex containing dichlorobenzene.

Yamaguchi, et al., U.S. Pat. No. 3,839,378 disclose the use of a palladium complex containing iodine or bromine and the use of hydrogen gas.

Cavinato et al., *J. Mol. Catalysis,* 10, 161–170 (1981), discuss effects of solvents on the hydrocarboalkoxylation of propylene with a palladium complex catalyst.

Hara, U.S. Pat. No. 3,793,369 discloses that it is desirable to employ a palladium complex with an aromatic tertiary phosphine, the molar ratio of the phosphine to palladium being 4:1 to 20:1.

von Kutepow, et al., U.S. Pat. No. 3,501,518, disclose carbonylation of olefins in the presence of metallic palladium or a palladium chalcogenide, a strong or medium strength acid (dissociation constant $K > 10^{-4}$) and an organic phosphine or nitrile. Sulfuric acid, perchloric acid, phosphoric acid and hydrogen halides are disclosed as useful acids. von Kutepow, et al., U.S. Pat. No. 3,437,676 disclose carbonylation of olefins in the presence of a complex palladium salt, e.g., bis(triphenylphosphine) palladium dichloride. The reaction may be carried out in the presence of an organic or inorganic acid such as sulfuric acid, phosphoric acid, boric acid, acetic acid, propionic acid, other carboxylic acids and hydrogen halides.

It is also known that carbonylation of olefins can proceed in the absence of a metal catalyst if a high concentration of a strong acid is employed. For example, Booth, et al., *J. Chem. Soc. Perkin* I. 2441–2446 (1979) and Norrell, U.S. Pat. No. 3,965,132 disclose improved yields when trifluoromethanesulfonic acid is employed instead of sulfuric acid.

It is an object of this invention to provide a process for carbonylation of olefins which process does not employ corrosive halides and which provides an increase in reaction rate in comparison with that achieved using known strong acids such as sulfuric acid.

DISCLOSURE OF THE INVENTION

For further comprehension of the invention, and of the objects and advantages thereof, reference may be made to the following further description and to the appended claims in which the level features of the invention are particularly set forth.

The invention resides in a process for the carbonylation of olefinically unsaturated compounds in which process the compounds are contacted and reacted with carbon monoxide and a hydroxylic compound in the presence of a catalytic amount of a catalyst system comprising an organic phosphine liganded palladium compound and a perfluorosulfonic acid at about 50° to about 150° C. for a time sufficient to effect reaction.

The carbonylation reaction is applicable to a wide variety of olefinically unsaturated compounds, including compounds with more than one ethylenic group and substituted compounds. At least two substituents of the olefinic group should be hydrogen, and the olefinic group should not be conjugated with other aliphatic unsaturated groups. Substituents which do not interfere with the carbonylation reaction include, e.g., aryl, alkoxy, alkoxycarbonyl, carboxyl, cyano, acyl and aroyl. Halo-substituted compounds may be employed provided that the halo- substituents are at least two carbon atoms removed from the olefinic double bond. Preferably the unsaturated compounds contain from 2 to 30 carbon atoms. Hydrocarbons with terminal olefinic groups are preferred.

Olefinically unsaturated compounds which may be carbonylated include, e.g., ethylene, propylene, butenes, pentenes, hexenes, octenes, decenes, tetradecenes, octadecenes, docosenes, 1,5-hexadiene, 1,9-decadiene, 4-vinylcyclohexene, methyl 10-undecenoate, 10-undecenoic acid, 10-undecene-1-ol, 5-hexene-2-one, 5-hexenenitrile and trans-1,4,9-decatriene.

Hydroxylic compounds which can be employed in the practice of this invention include water and primary and secondary alcohols which contain 1 to 4 hydroxyl groups, preferably 1, and which preferably contain from 1 to 10 carbon atoms. When an alcohol is employed in the carbonylation process, the product is an ester. When water is employed as the hydroxylic compound, a carboxylic acid is obtained as the carbonylation product. Particularly preferred hydroxylic compounds are saturated, aliphatic, monohydric primary and secondary alcohols which contain from 1 to 10 carbon atoms. Useful alcohols include, e.g., methanol, ethanol, propanol-1, propanol-2, butanol-1, pentanol-1, hexanol-1, β-methoxyethanol, benzyl alcohol, and neopentyl alcohol. It is preferred to employ alcohol or water in an amount stoichiometrically required to complete the reaction. Excess alcohol may be employed in the carbonylation process as a solvent.

The catalyst system comprises a zerovalent or divalent palladium compound, an organic phosphine ligand and a perfluorosulfonic acid. Palladium can be added to the reaction mixture in a variety of forms including, e.g., supported palladium such as palladium on carbon or silica, tetrakis(trialkylphosphine)- and tetrakis(- triarylphosphine)palladium (0) compounds, palladium salts of perfluorosulfonic acids such as the palladium salts of trifluoromethanesulfonic acid and of perfluorooctanesulfonic acid, aryl-phosphine liganded palladium salts of perfluorosulfonic acids and, preferably, palladium salts of perfluorosulfonic acid polymers.

In general, the palladium catalyst is employed in a molar ratio of olefinically unsaturated compound to palladium of about 100:1 to about 5000:1, preferably about 400:1 to about 3000:1. Larger ratios may provide too little catalyst to achieve rate enhancement, and smaller ratios are uneconomical with regard to palladium.

Use of perfluorosulfonic acids with organic phosphine liganded palladium compounds has been observed to result in an increase in the rate of reaction in comparison to reactions carried out using sulfuric acid. Useful organic phosphine ligands include, e.g., trialkylphosphines, triarylphosphines such as triphenylphosphine, tri-p-tolylphosphine and tri-m-tolylphosphine; and alkylarylphosphines such as ethyldiphenylphosphine, methyldipheylphosphine, propyldiphenylphosphine, and 1,6-hexamethylenebis(diphenylphosphine). In a small number of experimental reactions, it was observed that the reaction did not proceed satisfactorily when certain alkylarylphosphines, namely, 1,2-dimethylenebis(diphenylphosphine) and 1,4-tetramethylenebis(diphenylphosphine), were used. It is believed that this was due to intramolecular cyclization. The triarylphosphines, especially triphenylphosphine, are preferred.

Excess amounts of phosphine ligand over that required to form a complex with the palladium compound are preferred to stabilize the catalyst complex. A molar ratio of phosphorus to palladium of at least about 4:1 is especially preferred.

Perfluorosulfonic acids which can be employed include, e.g., trifluoromethanesulfonic acid, pentafluoroethanesulfonic acid, nonafluorobutanesulfonic acid, perfluorooctanesulfonic acid, and perfluorosulfonic acid polymers. Preferred are perfluorosulfonic acid polymers which have a number average molecular weight of at least about 5000. The polymer should contain a sufficient number of sulfonic acid groups to give an equivalent weight of about 500 to about 20,000, preferably about 900 to about 2000. Although the polymer backbone will largely comprise perfluorinated carbon atoms, it is not necessary that all other atoms be excluded. For example, ether oxygen may be present in the backbone or in the side chains of the polymer. Other atoms or groups such as hydrogen, chlorine and carboxyl groups may be present in limited amounts without significantly affecting the stability or operability of the polymer under the process conditions. It is preferred that the polymer contain no greater than about 5 weight percent total of such other atoms or groups. The perfluorosulfonic acid may be employed directly as an additive or as a preformed palladium salt of the acid.

Typically, the perfluorosulfonic acid is employed in a molar ratio of acid to palladium of about 1:1 to 50:1, preferably about 4:1 to 25:1.

Although a solvent is not required for the carbonylation reaction, it may be advantageous to employ one, particularly when higher molecular weight olefinically unsaturated compounds are employed as substrates. Alternatively, as noted above, an excess quantity of an alcohol reactant may be employed as a solvent. If a solvent is used, an important factor to be considered in the selection of one suitable for a particular carbonylation reaction, is the boiling point difference between the solvent and the carbonylated product. The boiling point difference should be such as to enable efficient separation of the solvent and product by simple distillation. Suitable solvents include aromatic hydrocarbons such as benzene, toluene and the xylenes, chlorinated aromatic hydrocarbons such as o-dichlorobenzene, and miscellaneous solvents such as acetonitrile and tetramethylenesulfone.

The carbonylation reaction of this invention is effected by heating the olefinically unsaturated compound, the hydroxylic compound, the palladium catalyst system, and the perfluorosulfonic acid in an atmosphere of carbon monoxide at a temperature of about 50° to about 150° C., preferably about 80 to about 120° C. Carbon monoxide pressures of about 0.1 to about 25 MPa or more can be used although it is preferred to employ pressures in the range of about 5 to about 15 MPa. The reaction may be run for as long as about 24 hours, but 0.5 to 5 hour reaction periods generally suffice and are preferred.

The process of the invention can be readily carried out using well-known chemical engineering practices which include continuous, semi-continuous and batch operations.

The type of reactor used in this invention is not critical as long as it is able to withstand the temperatures and pressures involved. Pressure vessels of high tensile steel are typically used, either lined or unlined. Suitable reactor liners include Hastelloy ® metals, stainless steel, silver, copper, tantalum, glass and glazed ceramics.

The reaction is carried out by charging the olefin, if liquid or solid, the hydroxylic compound, the catalyst system and any solvent into a suitable pressure-resistant vessel. For laboratory work, a shaker or rocker system is convenient for agitating the reactants and effecting intimate contact of the reactants. The charged reactor is closed, chilled in dry ice, evacuated and placed in a shaker or rocker. The olefinically unsaturated compound, if gaseous, is then added and the system is connected to a supply of carbon monoxide. Sufficient carbon monoxide is added to give the desired pressure at the chosen reaction temperature.

The system is then heated under agitation until reaction is complete. As the reaction proceeds, more carbon monoxide may be added periodically to maintain the pressure in the desired range. The course of the reaction is readily followed by observation of the drop in pressure. The product or products can be removed from the reaction mixture by conventional methods of isolation such as distillation.

EXAMPLES

The following are illustrative examples of the invention in which all parts and percentages are by mol, and all degrees are Celsius unless otherwise noted. Conversions were calculated by the equation: Conversion = mols ester/mols olefinically unsaturated compound charged. The reported relative amounts of iso-ester (iso) are mols isobutyrate/(mols isobutyrate + mols n-butyrate).

The amounts of total ester and iso- ester obtained were determined by a standard gas chromatographic procedure using a 10'×⅛" column of 10% SE-30 on 80/100 mesh diatomaceous earth. A temperature program of 110° (2 min) to 220° was utilized with a helium flow of about 30 ml/min. Response factors referenced against toluene (internal std) were employed to calculate the mols of products.

In the general carbonylation procedure employed, a 330 mL stainless steel shaker tube was flushed with nitrogen and charged with the palladium compounds, the arylphosphine, and the alcohol which contained the perfluorosulfonic acid. The tube was cooled to −78° C., and the specified quantity of olefinically unsaturated hydrocarbon was condensed into the tube. The tube was closed, connected to a pressure cell unless otherwise noted, and heated to the specific reaction temperature. Carbon monoxide was then added to the tube until the desired pressure was reached. The carbonylation reaction was carried out for 1 hr, and a pressure vs. time curve was recorded. The tube was cooled to room temperature, the reaction mixture was filtered to remove any solids, and the liquid product mixture was analyzed.

The pressure vs. time curve was used to measure the initial rate of carbonylation at low conversion of olefin. The initial rate was normalized for the number of moles of palladium initially charged. The units employed to define the initial turnover rate are mol ester/mol Pd/hr.

EXAMPLE 1

In this example, carbonylation of propylene was carried out at 105° and 13.8 MPa carbon monoxide pressure for 2 hrs by the general procedure except that a pressure cell was not employed. The tube was charged as follows:

1.0 mol propylene
1.5 mols methanol
11.5 mmols triphenylphosphine
1.29 mmols $[(C_6H_5)_3P]_4Pd$
2.25 mmols $CF_3SO_3H$.

As the reaction proceeded, additional carbon monoxide was added in increments to maintain the pressure at 13.8 MPa. No pressure drop occurred after the first hour of reaction. Conversion to product ester was 53.4% with a 30.8% iso content; 410 mol ester/mol Pd/hr.

EXAMPLES 2–4

In these examples, carbonylation of propylene was carried out at 100° and 13.8 MPa carbon monoxide pressure by the general procedure, as follows:

0.33 mol propylene
0.50 mol methanol
0.43 mmol $[(C_6H_5)_3P]_4Pd$
4.96 mmols triphenylphosphine.

The results, summarized in Table I, show an increased rate of reaction with added perfluorosulfonic acid compared with an equivalent protonic amount of the dibasic acid, sulfuric acid.

TABLE I

| | Homogeneous Catalyst | | | |
|---|---|---|---|---|
| Example | Acid, mol × 10³ | Conversion % | Iso, % | Mol ester/ mol Pd/hr |
| 2 | FC-95,(1) 2.26 | 37.5 | 28.9 | 678 |
| 3 | CF₃SO₃H, 2.27 | 47.4 | 28.9 | 828 |
| 4 | CF₃SO₃H, 9.07 | 92.5 | 32.7 | 1262 |
| Control A | H₂SO₄, 1.12 | 22.2 | 25.5 | 382 |

(1)FC-95 is $C_8F_{17}SO_3H$

EXAMPLES 5–8

In these examples, carbonylation of propylene was carried out at 13.8 MPa carbon monoxide pressure using a heterogeneous palladium catalyst by the general procedure, as follows:

0.33 mol propylene, unless otherwise noted
0.50 mol methanol
5 wt. % palladium-on-carbon; 0.43 mmol Pd
6.68 mmol triphenylphosphine.

The results, summarized in Table II, show an increased rate of reaction with added perfluorosulfonic acid compared with an equivalent protonic amount of the dibasic acid, sulfuric acid.

TABLE II

| Example | Acid, mol × 10³ | Temp | Conversion % | Iso, % | Mol ester/ mol Pd/hr |
|---|---|---|---|---|---|
| 5 | FC-95, 2.26 | 100 | 48.4 | 28.9 | 805 |
| 6 | CF₃SO₃H, 2.29 | 100 | 54.8 | 28.6 | 1498 |
| 7(1) | CF₃SO₃H, 2.27 | 100 | 37.5 | 29.7 | 845 |
| 8 | CF₃SO₃H, 2.27 | 80 | 21.9 | 25.0 | 295 |
| Control B | H₂SO₄, 1.14 | 100 | 26.2 | 27.3 | 349 |

(1)0.67 mol propylene was used

EXAMPLE 9

Carbonylation of propylene was carried out at 100° and 13.8 MPa carbon monoxide pressure by the general procedure, as follows:

0.33 mol propylene
0.50 mol methanol
0.43 mmol $[(C_6H_5)_3P]_4Pd$
4.96 mmol triphenylphosphine
PFIEP; 2.26 milliequivalents sulfonic acid group.

PFIEP is a Du Pont Nafion ® perfluorosulfonic acid polymer of equivalent weight 1100 as determined by titration of the sulfonic acid groups.

Carbonylation gave 23.1% conversion to reaction product which contained 27.6% iso ester product. The mol ester/mol Pd/hr was 719.

EXAMPLES 10–15

These examples illustrate the carbonylation reaction in which a palladium salt of a perfluorosulfonic acid polymer is employed as a catalyst. The catalyst was prepared by reaction of PFIEP (22.8 g; 20.1 milliequivalents sulfonic acid groups) with 2.32 g (9.04 mmol Pd) of Pd(NO₃)₂.XH₂O (41.3 wt. % Pd) at 60° for 1 hr with stirring. The reaction mixture was allowed to stand at room temperature for 11 days. The resin was separated by filtration, and the aqueous filtrate was titrated with 0.1 N sodium hydroxide for liberated nitric acid; 16.3 mmol. The resin was dried at 110° for 8 hrs under nitrogen to give 23.4 g of reddish-black product having 3.25 wt. % palladium (Catalyst A). Analogous procedures were employed to prepare resins which contained 1.34 wt. % palladium (Catalyst B) and 1.55 wt. % palladium (Catalyst C).

Carbonylation was carried out at 13.8 MPa carbon monoxide pressure by the general procedure, as follows:

0.33 mol propylene, unless otherwise noted.
0.50 mol methanol.
The results are summarized in Table III.

TABLE III

| Example | Pd Catalyst, mol × 10³ Pd | (C₆H₅)₃P, mol × 10³ | Temp, °C | Conversion % | Iso % | Mol ester/ mol Pd/hr |
|---|---|---|---|---|---|---|
| 10 | B, 0.13 | 6.68 | 100 | 22.2 | 26.9 | 1807 |
| 11 | C, 0.49 | 20.0 | 100 | 42.0 | 26.8 | 817 |
| 12 | A, 0.34 | 6.68 | 100 | 16.8 | 26.3 | 294 |
| 13[1] | A, 0.34 | 6.68 | 100 | 12.0 | 27.1 | 169 |
| 14 | C, 0.16 | 6.68 | 140 | 3.5 | 24.4 | 477 |
| 15 | A, 0.43 | 6.68 | 130 | 15.8 | 25.9 | 336 |

[1] 0.17 mol propylene was used

EXAMPLES 16-19

In these examples, carbonylation of a designated olefin was carried out at 100° and 13.8 MPa carbon monoxide pressure by the general procedure using in each example a homogeneous catalyst obtained from 0.43 mmol [(C₆H₅)₃P]₄Pd and 4.96 mmols triphenylphosphine. The results, summarized in Table IV, show an increased rate of reaction with added trifluoromethanesulfonic acid compared with an equivalent protonic amount of the diabasic acid, sulfuric acid.

EXAMPLE 20-22

In these examples the effect of carbon monoxide pressure on propylene carbonylation was studied at 100° using the general procedure, as follows:
 0.33 mol propylene
 0.50 mol methanol
 5 wt. % palladium-on-carbon; 0.43 mmol Pd
 6.68 mmol triphenylphosphine
 PFIEP; 2.26 milliequivalents sulfonic acid groups.
The results are summarized in Table V.

TABLE IV

| Ex. | Hydroxylic Compound, mols | Acid, mols × 10³ | Olefin, mols | Conversion % | Iso % | Mol ester/ mol Pd/hr |
|---|---|---|---|---|---|---|
| 16 | Ethanol 0.34 | CF₃SO₃H, 2.27 | Propylene, 0.33 | 53.9 | 25.6 | 666 |
| 17 | Methanol, 0.50 | CF₃SO₃H, 2.29 | Cis-2-Butene, 0.34 | 22.4 | 39.9[1] | 541 |
| 18 | Methanol, 0.50 | CF₃SO₃H, 2.29 | Cis-2-Butene, 0.34 | 26.5 | 38.9[1] | 552 |
| 19 | Water[2] 0.50 | CF₃SO₃H, 2.27 | Propylene, 0.33 | 1.1 | 24.3 | 23 |
| * | Ethanol, 0.34 | H₂SO₄, 1.12 | Propylene, 0.33 | 17.4 | 26.4 | 240 |
| ** | Methanol, 0.50 | H₂SO₄, 1.12 | Cis-2-Butene, 0.34 | 6.9 | 45.6[1] | 193 |
| *** | Water[2] 0.50 | H₂SO₄, 1.12 | Propylene, 0.33 | 0 | — | — |

[1] The products obtained were methyl 2-methylbutyrate (iso) and methyl valerate (n). Examples 17 and 18 are duplicate runs.
[2] Tetramethylenesulfone, 15 ml, was added as a solvent.
*Control C
**Control D
***Control E

TABLE V

| Example | CO Pressure (MPa) | Conversion, % | Iso, % | Mol ester mol Pd/hr |
|---|---|---|---|---|
| 20 | 6.9 | 28.4 | 29.0 | 252 |
| 21 | 13.8 | 28.5 | 28.2 | 353 |
| 22 | 20.7 | 16.4 | 27.8 | 250 |

EXAMPLES 23-24

In these examples the bisphosphine ligand, (C₆H₅)₂P(CH₂)₆P(C₆H₅)₂, was employed. Carbonylation of propylene was carried out at 100° and 13.8 MPa carbon monoxide pressure by the general procedure, as follows:
 0.33 mol propylene
 0.50 mol methanol
 3.3 mmol (C₆H₅)₂P(CH₂)₆P(C₆H₅)₂.

The results, summarized in Table VI, show an increased rate of reaction with an added perfluorosulfonic acid compared with an equivalent protonic amount of the dibasic acid, sulfuric acid.

TABLE VI

| Example | Pd Catalyst, mol × 10³ Pd | Acid, mol × 10³ | Conversion % | Iso % | Mol ester/ mol Pd/hr |
|---|---|---|---|---|---|
| 23 | 5 wt. % Pd/C; 0.43 | CF₃SO₃H, 2.27 | 7.7 | 16.9 | 128 |
| 24 | Ex. 12, Cat. A; 0.43 | — | 8.4 | 16.7 | 226 |
| Control F | 5 wt. % Pd/C; 0.43 | H₂SO₄, 1.12 | 5.2 | 16.9 | 72 |

EXAMPLE 25

In this example, carbonylation of propylene was carried out at 100° and 13.8 MPa carbon monoxide pressure for 2 hrs by the general procedure except that a pressure cell was not employed. The tube was charged as follows:
 1.0 mol propylene
 1.5 mol methanol
 15.3 mmols triphenylphosphine
 0.75 mmol Pd as the palladium salt
 (3.95 wt. % Pd) of PFIEP, prepared by the procedure described in Examples 10–15.

As the reaction proceeded, additional carbon monoxide was added in increments to maintain the pressure at 13.8 MPa. No pressure drop occurred after the first 30 min of the reaction. Conversion to product ester was 22.3% with a 29.3% iso content; 599 mol ester/mol Pd/hr.

BEST MODE FOR CARRYING OUT THE INVENTION

The best mode contemplated by the applicant for carrying out his invention is described by Examples 3, 6, 9 and 10 which show large increases in reaction rates.

INDUSTRIAL APPLICABILITY

Esters are a well-known class of useful organic compounds. Many esters are useful as solvents, and as plasticizers for polymers. Some esters are useful in perfumes, essences, and flavoring agents. Diesters and additionally useful for making polymers, such as polyesters and polyamides.

Carboxylic acids which can be made by the process of this invention are also well knwon to have a variety of uses. Higher molecular weight acids can be used in detergent compositions. Many low molecular weight acids, and particularly salts thereof, are useful as preservatives, as buffering agents, and as solvents. Acids are also extremely important intermediates for the manufacture of ketones, amides, esters, nitriles and many other organic compounds.

While the preferred embodiments of the invention are disclosed by the above, it is to be understood that the invention is not limited to the precise constructions herein disclosed and that the right to all modifications coming within the scope of the following claims is reserved.

I claim:

1. In an improved catalytic carbonylation process for preparing acids and esters by reacting an olefinically unsaturated compound, carbon monoxide and a hydroxylic compound, at about 50° to about 150° C., in the presence of a catalyst comprising an organic phosphine liganded palladium compound and an acid, wherein the improvement comprises using a perfluorosulfonic acid as the acid.

2. Process of claim 1 wherein the olefinically unsaturated compounds are nonconjugated hydrocarbons and contain 2 to 30 carbon atoms including a terminal olefinic group and the hydroxylic compound is water or a primary or secondary alcohol which contains 1 to 10 carbon atoms and 1 to 4 hydroxyl groups.

3. Process of claim 2 wherein the palladium is added to the reaction mixture as supported palladium, a tetrakis(trialkylphosphine)- or tetrakis(triarylphosphine) palladium compound, a palladium salt of a perfluorosulfonic acid, an arylphosphine liganded palladium salt of a perfluorosulfonic acid, or a palladium salt of a perfluorosulfonic acid polymer.

4. Process of claim 2 wherein the organic phosphine is a trialkylphosphine, a triarylphosphine, or an alkylarylphosphine.

5. Process of claim 2 wherein the organic phosphine ligand is triphenylphosphine, tri-p-tolylphosphine, tri-m-tolylphosphine, ethyldiphenylphosphine, methyldiphenylphosphine, propyldiphenylphosphine or 1,6-hexamethylenebis(diphenylphosphine).

6. Process of claim 2 wherein the perfluorosulfonic acid is trifluoromethanesulfonic acid, pentafluoroethanesulfonic acid, nonafluorobutanesulfonic acid, perfluorooctanesulfonic acid or a perfluorosulfonic acid polymer.

7. Process of claim 2 wherein the acid is trifluoromethanesulfonic acid.

8. Process of claim 2 wherein the acid is perfluorooctanesulfonic acid.

9. Process of claim 2 wherein the acid is a perfluorosulfonic acid polymer.

10. Process of claim 9 wherein the perfluorosulfonic acid polymer has a number average molecular weight of at least 5,000 and an equivalent weight of 500 to 20,000.

11. Process of claim 10 wherein the molar ratio of phosphorus to palladium is at least 4 to 1; the molar ratio of olefinically unsaturated compound to palladium is about 100:1 to 5,000:1; the molar ratio of acid to palladium is about 1:1 to 50:1; the partial pressure of carbon monoxide is about 0.1 to about 25 MPa; and the amount of hydroxylic compound is at least the amount stoichiometrically required to complete the reaction.

12. Process of claim 11 wherein the olefinically unsaturated compound is propylene and the hydroxylic compound is methanol.

13. Process of claim 12 wherein the palladium is added to the reaction mixture as a salt of a perfluorosulfonic acid polymer and the orgnic phosphine is triphenylphosphine.

14. Process of claim 13 wherein the perfluorosulfonic acid polymer has an equivalent weight of about 900 to about 2000 and contains less than 5 weight percent of hydrogen, chlorine and carboxyl groups, the molar ratio of olefin to palladium is 400:1 to 3000:1, and the temperature is 80° to 120° C.

* * * * *